United States Patent [19]
Berki et al.

[11] Patent Number: 5,902,302
[45] Date of Patent: May 11, 1999

[54] ACCESSORY DEVICE FOR AN ORTHOPEDIC FIXATOR

[75] Inventors: Sandor Berki, Szeged, Hungary; Giovanni Faccioli, Monzambano; Daniele Venturini, Povegliano Veronese, both of Italy

[73] Assignee: Orthofix S.r.l., Bussolengo, Italy

[21] Appl. No.: 09/003,618

[22] Filed: Jan. 7, 1998

Related U.S. Application Data

[62] Division of application No. 08/566,063, Dec. 1, 1995, Pat. No. 5,707,370.

[30] Foreign Application Priority Data

Sep. 19, 1995 [IT] Italy .................................. VR95A0076

[51] Int. Cl.$^6$ .................................................. A61B 17/64
[52] U.S. Cl. ............................................. 606/59; 606/55
[58] Field of Search .................................. 606/54, 55, 57, 606/58, 59, 64

[56] References Cited

U.S. PATENT DOCUMENTS

Re. 34,985  6/1995  Pennig ...................................... 606/58

*Primary Examiner*—Michael Buiz
*Assistant Examiner*—David O. Reip
*Attorney, Agent, or Firm*—Hopgood, Calimafde, Kalil & Judlowe

[57] ABSTRACT

A preferred embodiment of the invention provides an accessory device which is removably applicable to a double ball-jointed fixator, to assume the relation of a cage that effectively surrounds both ball-joints of the fixator. One longitudinal end of the accessory cage quickly mounts to one bone-screw mounting member of the fixator and establishes first intersecting orthogonally related articulation axes of a first half of a dual Cardan joint, wherein such first intersection is coincident with the ball center of a first ball-joint of the fixator; the other longitudinal end of the accessory cage quickly mounts to the other bone-screw mounting member of the fixator and establishes second intersecting orthogonally related articulation axes of a second half of the dual Cardan joint, with such second intersection coincident with the ball center of the second ball-joint of the fixator. A bridle or bridge connector having spaced end connections to corresponding elements of the respective halves of the dual Cardan joint establishes a fixed spacing between the orthogonal-axis intersection points of the respective halves of the dual Cardan joint, and this fixed spacing is identical to the fixed spacing between ball centers of the double ball-jointed fixator. The releasable mounting of each half of the cage structure to its bone-screw mounting member of the fixator is a releasably clampable rotatable mount, wherein rotatability is about a longitudinal axis of the bone-screw mount of the fixator, and wherein the same longitudinal axis is aligned with the associated ball center. Individual clamp action is thus provided for independent adjustment of accessory-cage components about each of three articulation axes, for each of the halves of the dual Cardan joint.

9 Claims, 2 Drawing Sheets

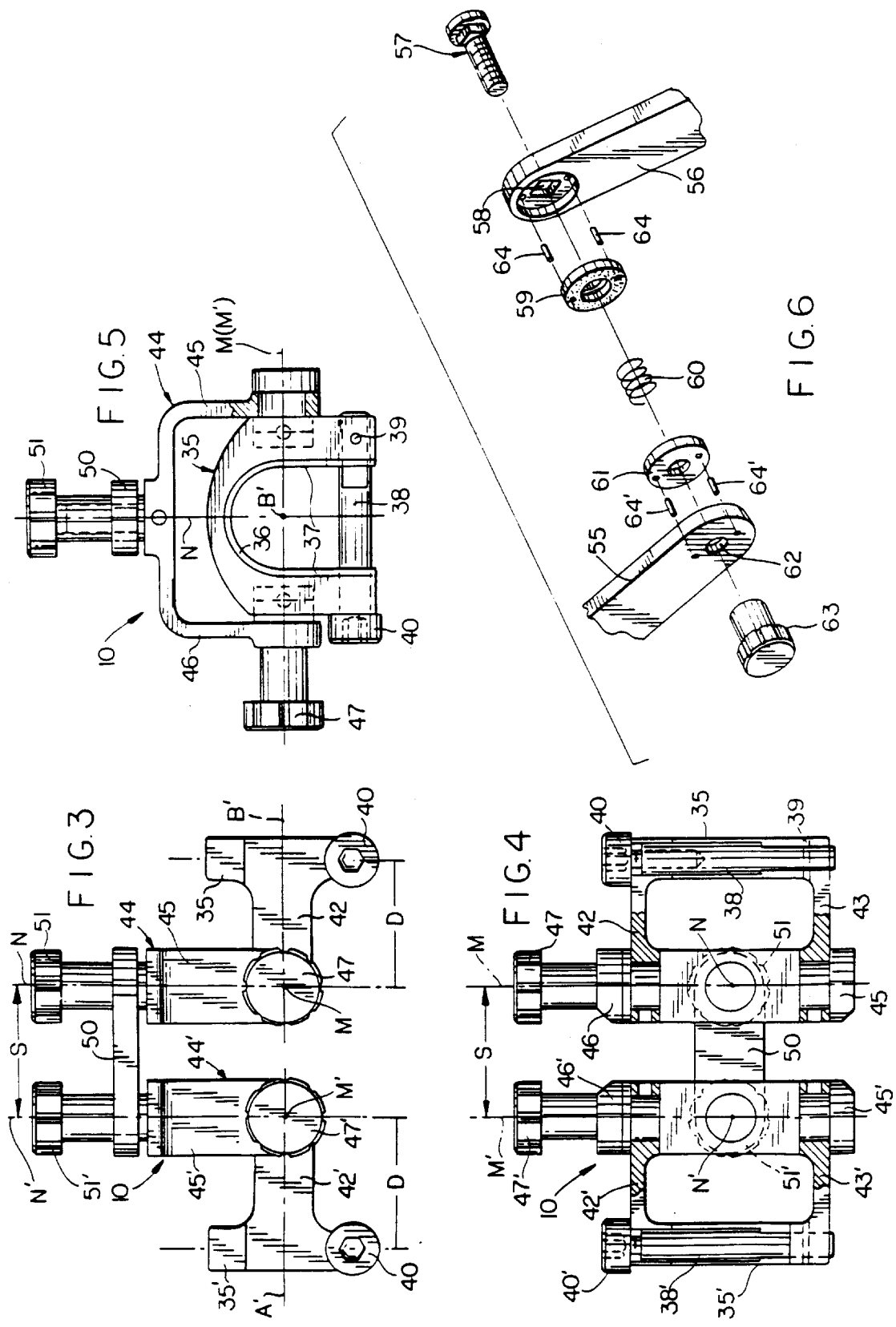

ACCESSORY DEVICE FOR AN ORTHOPEDIC FIXATOR

This application is a division of application Ser. No. 08/566,063, filed Dec. 1, 1995, now U.S. Pat. No. 5,707,370, being directed to subject matter cancelled without prejudice in said copending application.

BACKGROUND OF THE INVENTION

The invention relates to external fixators, and in particular to a bone-fixator configuration wherein spaced first and second bone-screw mounting members are connected end-to-end via one or more ball-and-socket joints which are releasably lockable to preserve a given orientation of one mounting member to the other mounting member.

U.S. Pat. No. 4,988,349 (now reissue U.S. Pat. No. Re. 34,985) describes an external fixator of the character indicated, having particular application to the fixation of fragments of a fractured bone associated with the wrist. Such fractures are complex, and it is unnecessarily difficult to resort to internal fixation techniques. Moreover, the external fixation of such fractures is also tedious, if the surgeon is to achieve and fix a precise fit of the fracture ends to each other. Said patent partially solves the problem by providing a central spacer element, each end of which has releasably lockable universal ball-joint connection to the end of a different one of the respective bone-screw mounting members.

But each ball-joint connection has universal action, and it is awkward, and in some cases difficult, to make a correctly oriented and clamped setting of each ball-joint, to best serve the surgeon's purposes in fixation of a given wrist-related fracture, particularly if limited wrist articulation is to be afforded during part of the period for fracture healing.

Brief Statement of the Invention

It is an object of the invention to provide an accessory device for a ball-jointed fixator of the character indicated, whereby precise adjustments may be individually made in each of several specific axes of articulated connection, while ball-joint locking mechanism is unclamped to an extent that articulation is determined solely by adjustment via the accessory device.

Another object is to meet the above object with provision for removable fastening of the accessory device to the fixator only as long as needed to develop an oriented relation of bone-mounted fixator ends to each other, so that the orthopedic surgeon can be satisfied (i) as to the correct fit of fractured-bone fragments to each other, and (ii) as to location of a distal ball-joint center in the frontal plane through the hand and on the axis of wrist articulation of said plane at the distal ends of the radius and ulna, whereupon to enable him to clamp the ball-joint locking mechanism and then to remove the accessory device.

A specific object is to achieve the above objects with an accessory device which is applicable to a fixator having fixedly spaced ball-joint connections to the respective bone-screw mounts of a double-jointed external fixator.

A general object is to meet the above objects with an accessory device of basic simplicity and minimum bulk, affording the surgeon maximum access to adjustable elements of the fixator to which it is to be removably applied.

In its presently preferred embodiment, the invention achieves the foregoing objects with an accessory device which is unit-handling and which is readily applied to a double ball-jointed fixator, to assume the relation of a cage that effectively surrounds both ball-joints of the fixator. One longitudinal end of the accessory cage quickly mounts to one bone-screw mounting member of the fixator and establishes first intersecting orthogonally related articulation axes of a first half of a dual Cardan joint, wherein such first intersection is coincident with the ball center of a first ball-joint of the fixator; the other longitudinal end of the accessory cage quickly mounts to the other bone-screw mounting member of the fixator and establishes second intersecting orthogonally related articulation axes of a second half of the dual Cardan joint, with such second intersection coincident with the ball center of the second ball-joint of the fixator. A bridle or bridge connector having spaced end connections to corresponding elements of the respective halves of the dual Cardan joint establishes a fixed spacing between the orthogonal-axis intersection points of the respective halves of the dual Cardan joint, and this fixed spacing is identical to the fixed spacing between ball centers of the double ball-jointed fixator. The releasable mounting of each half of the cage structure to its bone-screw mounting member of the fixator is a releasably clampable rotatable mount, wherein rotatability is about a longitudinal axis of the bone-screw mount of the fixator, and wherein the same longitudinal axis is aligned with the associated ball center. Individual clamp action is thus provided for independent adjustment of accessory-cage components about each of three articulation axes, for each of the halves of the dual Cardan joint.

BRIEF DESCRIPTION OF THE DRAWINGS.

A preferred embodiment of the invention will be described in detail in conjunction with the accompanying drawings, in which:

FIG. 3 is an enlarged view in side elevation of the cage accessory of FIG. 1;

FIG. 4 is a bottom view, partially in section, generally on the alignment 4—4 of FIG. 3;

FIG. 5 is a right-end view of the structure of FIG. 3; and

FIG. 6 is an exploded view in perspective, illustrative of one of a plurality of different releasable clamp mechanisms in the cage accessory of FIGS. 3 to 5.

DETAILED DESCRIPTION

Figure 1:
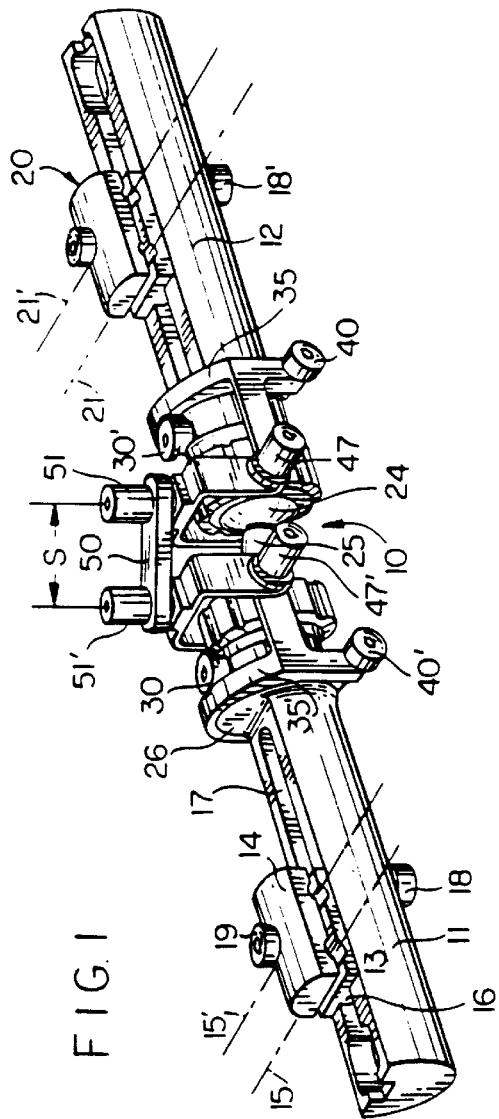
FIG. 1 is a perspective view of a cage-accessory structure of the invention, in assembled relation to a double ball-jointed external fixator.
Figure 2:
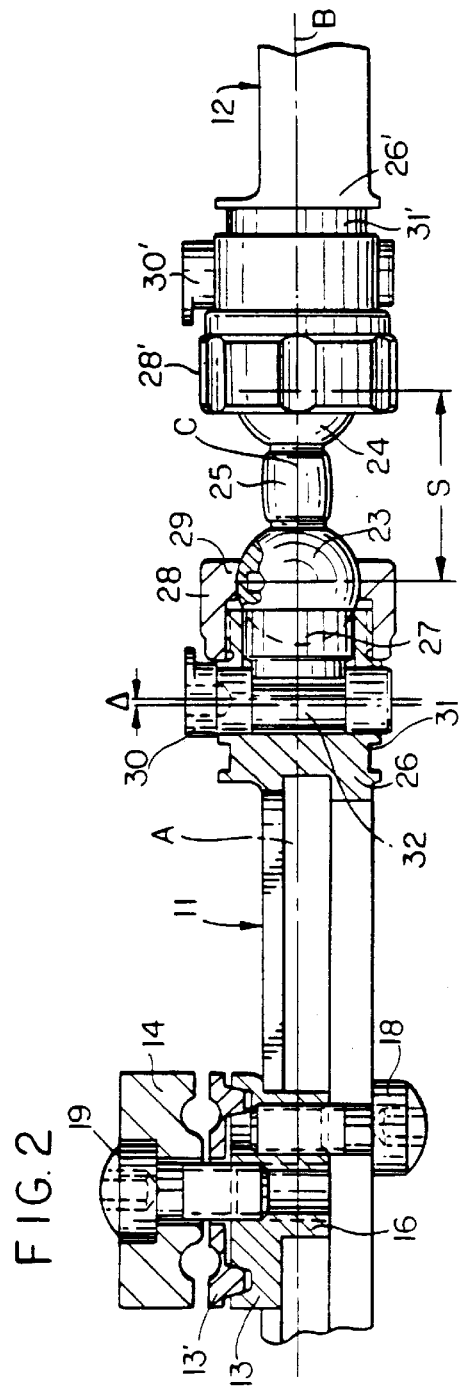
FIG. 2 is an enlarged fragmentary side elevation of the fixator of FIG. 1, without the cage structure of FIG. 1.

In FIG. 1, accessory cage structure 10 of the invention is shown in assembled relation to a double ball-joint orthopedic fixator, detail of which best appears in FIG. 2. This fixator comprises first and second elongate bone-screw mounting members 11, 12. In the case of mounting member 11, a slide element 13 and a clamp element 14 have confronting faces that are transversely grooved for accommodation of bone screws or pins (not shown) on spaced parallel axes 15, 15'. The underside of slide element 13 is an elongate rib or tongue 16 which engages a longitudinal guide slot 17, for longitudinally adjusted positioning on axis A of member 11. A clamp bolt 18 passes through slot 17 for engagement with slide element 13 to releasably secure a selected longitudinal position, and another clamp bolt 19 releasably secures clamp element 14 to slide 13, with clamp action on bone screws or pins on axes 15, 15'. Greater detail in FIG. 2 enables identification of an intermediate component of the bone-screw clamp, namely a plate 13' which is grooved for bone-screw engagement and which is also guided by a downward annular rib, engaging an annular groove in slide 13, thereby permitting an angular range of adjustability of the orientation of bone-screw grooves about the axis of clamp bolt 19.

At the other end of the fixator, the mounting member 12 will be seen in FIG. 1 to carry similarly adjustable and releasably clamped slide structure 20 which therefore needs no further description, it being understood that bone screws or pins clamped at 20 on axes 21, 21' may serve a bone element other than a different element, e.g. of the same fractured wrist, served on axes 15, 15'. And the longitudinal axis of member 12 and, therefore, of slide-20 adjustability is indicated at B.

The double ball-joint which interconnects confronting head ends of mounting members 11, 12 is shown to comprise two ball elements 23, 24 with a reduced rod-like connection 25 which determines a fixed spacing S between centers of the ball elements; the rod-like connection 25 has symmetry about a central longitudinal axis C through both ball centers. Socket structures of the confronting head ends of members 11, 12 have concave spherical formations which respectively engage the ball formations 23, 24. In the case of head end 26 of member 11, a cylindrical clamp element 27 is longitudinally guided by a bore in head end 26, concentric with longitudinal axis A; clamp element 27 has a concave spherical end face for ball-23 engagement, and an annular clamping element 28, threadedly retained to head end 26, has a radially inward outer-end flange 29 with an inner surface that is also a concave annular portion of a sphere, for axial retention and capture of ball 23 at the head end 26. A transverse pin 30, having an eccentric formation 32, is journalled for externally accessed wrench rotation, to eccentrically displace clamp element 27 into axially clamped action on ball 23, the same being a squeeze action between oppositely dished concave portions of a sphere, in the flange 29 of ring 28 and in the end face of element 27. It is noted that the threaded drive of ring 28 to head end 26 is not a clamping engagement but merely an assembly engagement, in that pin 30 rotation is needed for the eccentric displacement $\Delta$ to achieve a locking of mounting element 11 to ball 23.

The releasably secured engagement of head end 26' of mounting member 12 to the other ball 24 of the connector is precisely as described for mounting-member 11 engagement to ball 23, and corresponding parts are identified by the same reference numbers, having primed notation.

What has thus far been described for the double ball-jointed fixator of FIGS. 1 and 2 is the present commercially available "wrist fixator", Model 35.000, of Orthofix S.r.l., Verona, Italy. For use with the accessory cage 10 of the invention, there is but a single simple modification of this commercial fixator, namely, to incrementally and longitudinally elongate the head end 26 (26') of the respective mounting members 11, 12, to the extent necessary to provide a circumferentially continuous groove 31 (31') at each of the respective head ends 26 (26'). Said groove 31 (31') can be referred to as a bearing formation that defines a circular rotary support at longitudinal offset from the associated ball-joint connection and that is centered on the longitudinal axis of the mounting member 11 (12).

Referring now to FIGS. 3, 4 and 5 in addition to FIG. 1, the cage construction of the invention is defined by and between two similarly arched or U-shaped members 35 (35'), each having an inner semicircular profile or rib 36 designed for accurate fit to and location by one of the grooves 31, 31'. The arched or U-shape continues with parallel side walls or forked arms and inward rib formations 37, to an open end which is selectively openable/closable by means of a rod 38 that is pivotable about a pin connection 39 to one of the forked arms of the U-shape. Rod 38 may be of two-piece construction wherein, as best seen in FIG. 4, the outer end of rod 38 has a threaded bore that accommodates a clamp bolt 40. When bolt 40 is loosened, it clears the opposite arm of the U-shape and permits a full 90° swing about pin 39, to fully open the arch of the U-shape, thus permitting lateral access of the U-shape for circumferential fit to head end 26' of mounting member 12, with at least a 180° engagement of rib 36 to groove 31'. Upon swinging rod 38 back to its closure position (see FIGS. 4 and 5), rod 38 has guided tangential contact with the sidewalls of groove 31', and this closed position fully stabilizes orientation of the U-shape, throughout a full 360° range of rotational adjustment of member 35 about the longitudinal axis B of mounting member 12. A given angular setting of such rotational adjustment is secured by driving bolt 40 into a sufficiently squeezing displacement of the parallel arms and rib, into a tightened engagement with the applicable one of grooves 31, 31'.

Each of the similarly arched or U-shaped members 35 (35') further integrally includes two spaced parallel arms 42 (42'), 43 (43') which provide a longitudinal offset D such that, when assembled to the applicable one of grooves 31 (31'), laterally spaced bearings are established on a first transverse axis M (M') of Cardan-joint articulation. It will be understood that the offsets D are such as to geometrically align axes M (M') through the respective ball-joint centers and perpendicular to the respective longitudinal axes A', B' of members 35 (35') and that when in clamped assembly to grooves 31 (31'), the axes A', B' of members 35 (35') are coincident with the respective longitudinal axes A, B of the bone-screw mounting members 11, 12.

A second arched or U-shaped member 44 (44') has spaced arms 45 (45'), 46 (46') having pinned connection to the respective arms 42 (42'), 43 (43') to enable pivoted articulation of members 44 (44') about the respective axes M (M'). A knob 47 (47') on each of axes M (M') and at the location of pinned connection of arms 42 (42') to arms 46 (46') will be understood to be manually operable for selective locking and release of independently adjusted angular relationships about the first articulation axis M of a first Cardan-joint connection and about the first articulation axis M' of a second Cardan-joint connection.

Each of the second arched or U-shaped members 44 (44') provides a bearing for a second axis N (N') of Cardan-joint articulation wherein each axis N (N') is orthogonal to and intersects the first axis M (M') and is also aligned for passage through its associated ball-joint center. And a bridging element 50 provides pinned connection between the second arched or U-shaped members 44 (44'), at a fixed spacing S between the second articulation axes N (N'), with separate knobs 51 (51') to selectively secure adjusted angular relationships between bridge 50 and member 44 about axis N, and between bridge 50 and member 44' about axis N'. The fixed spacing S between articulation axes N, N' will be observed to be the same as the spacing between ball-joint centers of the fixation; thus, necessarily axes N, N' intersect their respective ball-joint centers, regardless of the adjusted angular orientation of bridging element 50 with respect to the U-shaped members 44, 44'.

The various knob-locking adjustments at 47, 47', 51 and 51' may be of a variety, such that each is available for independent selective locking of the pivoted adjustment of one member with respect to another member, as for example, bridging element 50 with respect to one of the U-shaped members 44 (44') about one of the axes N (N'), or one of the U-shaped members 44 (44') with respect to its associated other U-shaped member 35 (35') about an involved one of the axes M (M'). By way of illustration, the exploded view of FIG. 6 schematically depicts such a knob-actuated locking mechanism wherein two arms 55, 56 are to be locked and/or selectively adjusted for their relative angular relationship about a common pivot axis. A bolt 57 has keyed engagement to the bore 58 of arm 56, and passes through aligned bores in friction disc 59, a coil spring 60, another friction disc 61, and a bore 62 in arm 55, for adjustably threaded engagement to the threaded bore of knob 63. Each of the friction discs 59 (61) is seated in a counterbore of its arm 56 (55), being secured against rotation by rivets, suggested at 64 (64'). A tightening of knob 63 squeezes spring 60 and compresses the friction surfaces of discs 59, 61 against each other, to hold an adjusted angle between arms 55, 56; and, upon unthreading release of the friction engagement, by reason spring (60) action, the arms 55, 56 become available for selective angular readjustment.

In use, bone screws are set in pairs for fixator clamping at 15, 15' and at 21, 21', with slide clamps 18, 18' relaxed, and with ball-joint clamps 30, 30' backed off to permit universal adaptation of the axes A, B, C to each other. The cage structure 10 is then applied to the fixator, with all clamp knobs relaxed and with rods 38, 38' swung out, to permit lateral insertion at each of the groove locations 31, 31', whereupon rods 38, 38' are swung back to complete circumferential retention of each U-shaped member 35 (35'); at this point, clamp actuation of rods 38, 38' should not be driven, in order that rotational freedom with respect to the bone-screw mounts can remain for adjustment purposes. In the case of fixator application to set a fractured wrist, the fixator can be manipulated longitudinally so as to approximately register one of the ball-joint centers on the axis of articulation of the hand about the distal ends of the radius and ulna, whereupon the fixator-slide clamps may be set at 18, 18', and all the clamps of cage structure 10 may be tentatively set, with the ball-joint clamps 30, 30' relaxed. Now, with the aid of X-ray viewing from selected aspects, it can first be determined at what orientation to set the clamps 40, 40' of cage rotary adjustment about axes A, B, preparatory to individual adjustment and clamping about each of the axes M, M' and N, N' as necessary to satisfy the surgeon that the fracture has been correctly set. And only when thus satisfied as to all orientations set by all the cage clamps, is it appropriate to set the ball-joint clamps 30, 30', and to free the cage clamps (specifically clamps 40, 40') thus permitting a laterally displacing disassembly of cage structure 10 from the correctly set fixator. At a later time, when the surgeon determines that the patient can safely resume wrist action about the axis at the distal ends of the radius and ulna, the appropriate ball-joint clamp on said axis can be freed from clamping while the fracture-healing process continues as to fixator-retained components. Still later, when the healing process is determined to be sufficiently complete, the fixator and its bone screws can be readily removed, on an out-patient basis.

The described invention will be seen to achieve all stated objects. The cage 10 is a relatively open structure which provides access to significant components of the fixator, both for X-ray viewing from a variety of aspects, as needed for proper installation and for periodic inspection in the course of fracture healing. And the cage 10 affords not only the simplifying convenience of being able to correctly set the fixator by observing and adjusting for one component at a time, but also of assuring that when the fixator ball-joints are set, they are correctly set, including a correct setting for wrist-articulation about the distal ends of the radius and ulna, at a time significantly within and short of the full term required for fracture healing prior to fixator removal.

The described cage structure 10 may be manufactured and sold as a unit, for use with a fixator as described in detail in connection with FIG. 2. Alternatively, the cage structure 10 may be part of a kit which also includes one or more fixators as described in connection with FIG. 2. Still further, the fixator itself as described in connection with FIG. 2 may be an independent article of commerce, for those surgeons or hospitals that are already sufficiently supplied with cage structures as described.

In view of the correspondence between gimbal suspensions and certain elements of the described Cardan-joint structures, it is convenient sometimes to refer to the means of establishing rotational adjustment about axes M, M' and N, N' as gimbal suspensions, even though these suspensions are, as in the case of U-shaped members 35 (35') and 44 (44') only partially embracing of the members they interconnect. The main point is that each axis of cage articulation is independently settable for clamping or for selective rotary adjustment. And the entire cage structure is bodily removable from the fixator, once each component of angular adjustment has been completed.

What is claimed is:

1. An accessory device for a bone fixator having first and second elongate bone-screw-mounting bodies with releasably clampable ball-joint connection of adjacent longitudinal ends of said bodies for releasably clamping a selected orientation of said bodies about a geometric center of ball-joint connection, each of said bodies having a longitudinal axis aligned with its center of ball-joint connection;

said device comprising cage structure adapted for removable application to said fixator to define an elongate Cardan-joint connection formed at its respective ends for rotatable connection to the respective ends of said bodies with releasably clampable rotation about the respective longitudinal axes of said bodies, said Cardan-joint connection providing two orthogonally related articulation axes which intersect at the geometric center of ball-joint connection when said device is applied to said fixator, and separate releasably clampable means associated with each of the orthogonally related articulation axes of said Cardan-joint connection.

2. A bone fixator comprising first and second elongate bone-screw-mounting bodies with adjacent ends in spaced array, each of said bodies having a central longitudinal axis and bone-screw-mounting means adjustably securable along said longitudinal axis, a rigid connector having ball-joint connection at each of its ends to one of the adjacent ends of said bodies on each of the longitudinal axes of the respective bone-screw-mounting bodies, each ball-joint connection having means for releasably clamping a selected orientation of its elongate body with respect to said connector and about the geometric center of its ball-joint connection, and a rotary-bearing formation comprising a circumferential groove formed about an external surface of each of said bodies at longitudinal offset from the ball-joint connection end of each said body and centered about the longitudinal axis of each said body, each of said rotary-bearing formations defining a circumferentially continuous circular support for an accessory device.

3. The bone fixator of claim 2, in which the second of said bodies has a similar rotary-bearing formation at longitudinal offset from the ball-joint connection end of said second body.

4. The bone fixator of claim 2, in which each said rotary-bearing formation is longitudinally between the bone-screw-mounting means and the ball-joint connection end of its body.

5. The bone fixator of claim 2, in which said bone-screw-mounting means includes means for selective adjustment and clamping of one or more bone screws at a selected angular orientation with respect to the longitudinal axis of said one elongate body.

6. The bone fixator of claim 2, in which said rigid connector comprises two balls with a rigid connection of said balls in spaced relation, each of said balls being a component of a different one of said ball-joint connections.

7. A bone fixator system comprising:

first and second elongate bone-screw-mounting bodies with adjacent ends in spaced array, each of said bodies having a central longitudinal axis and bone-screw-mounting means adjustably securable along said longitudinal axis;

a rigid connector having ball-joint connection at each of its ends to one of the adjacent ends of said bodies on each of the longitudinal axes of the respective bone-screw-mounting bodies, each ball-joint connection having means for releasably clamping a selected orientation of its elongate body with respect to said connector and about the geometric center of its ball-joint connection;

a rotary-bearing formation comprising a circumferential groove formed about an external surface of each of said bodies at longitudinal offset from the ball-joint connection end of each said body, each of said rotary-bearing formations defining a circumferentially continuous circular support that is centered on the longitudinal axis of its body; and selectively settable means for limiting freedom of articulation to one axis of articulation to the exclusion of another one or more axes of articulation of said ball-joint connections, said selectively settable means comprising cage structure removably applicable to said bodies to define a dual Cardan-joint adapted for rotatable connection at its respective ends to the respective rotary-bearing formations of said bodies, said dual Cardan-joint providing (1) a first two orthogonal articulation axes which intersect at one of the geometric centers of ball-joint connection and (2) a second two orthogonal articulation axes which intersect at the other of the geometric centers of ball-joint connection, and separate releasably clampable means associated with each articulation axis and with each of the rotatable Cardan-joint connections to the respective rotary-bearing supports of said bodies.

8. A bone fixator system comprising:

first and second elongate bone-screw-mounting bodies with adjacent ends in spaced array, each of said bodies having a central longitudinal axis and bone-screw-mounting means adjustably securable along said longitudinal axis;

a rigid connector having ball-joint connection at each of its ends to one of the adjacent ends of said bodies on each of the longitudinal axes of the respective bone-screw-mounting bodies, each ball-joint connection having means for releasably clamping a selected orientation of its elongate body with respect to said connector and about the geometric center of its ball-joint connection;

cage structure removably applicable to said bodies to define a dual Cardan-joint adapted for separate rotatable connection at one of its respective ends to and around one of said bodies and at the other of its respective ends to and around the other of said bodies, each separate rotatable connection comprising a body formation coacting with a Cardan-joint-end formation, wherein an inner annular surface of a Cardan-joint end and an external annular body surface are separably engageable to define a rotary bearing that is centered on and at longitudinal offset from the ball-joint-connection end of the longitudinal axis of the coacting body, whereby the rotary-bearing connections to the respective ends of the dual Cardan-joint establish first and second rotary-adjustment axes which are also the respective longitudinal axes of said bodies;

said dual Cardan-joint providing (1) a first two orthogonal articulation axes which intersect at one of the geometric centers of ball-joint connection and (2) a second two orthogonal articulation axes which intersect at the other of the geometric centers of ball-joint connection; and separate releasably clampable means associated with each articulation axis and with each of the rotary-adjustment axes of Cardan-joint connection to the respective bodies.

9. The system of claim 8, in which the external body surface of rotary connection to a Cardan-joint end is a circumferential groove, and in which the coacting inner annular surface of a Cardan-joint end includes an arcuate rib engageable in said groove.

* * * * *